(12) United States Patent
Cox (10) Patent No.: US 6,179,867 B1
(45) Date of Patent: *Jan. 30, 2001

(54) FLEXIBLE STENT AND METHOD OF USE

(75) Inventor: Daniel L. Cox, Palo Alto, CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/008,366

(22) Filed: Jan. 16, 1998

(51) Int. Cl.⁷ ....................................................... A61F 2/06
(52) U.S. Cl. ........................................ 623/1.15; 623/1.17
(58) Field of Search ................................ 623/1, 12, 1.15, 623/1.16, 1.17; 606/192, 194, 195, 108

(56) References Cited

U.S. PATENT DOCUMENTS

| | | | |
|---|---|---|---|
| 5,383,892 | * | 1/1995 | Cardon et al. ........................ 606/198 |
| 5,395,390 | * | 3/1995 | Simon et al. ........................ 606/198 |
| 5,514,154 | * | 5/1996 | Lav et al. .............................. 623/12 |
| 5,549,663 | * | 8/1996 | Cottone, Jr. ............................ 623/1 |
| 5,575,818 | * | 11/1996 | Pinchuk .................................. 623/1 |
| 5,716,393 | * | 2/1998 | Lindenberg et al. ................... 623/1 |
| 5,741,327 | * | 4/1998 | Frantzen ................................. 623/1 |
| 5,911,732 | * | 6/1999 | Hojeibane ............................ 606/194 |

FOREIGN PATENT DOCUMENTS

| | | |
|---|---|---|
| WO 97/25937 | 7/1997 | (WO) . |
| 98/22159 | 11/1997 | (WO) . |
| WO 99/17680 | 4/1999 | (WO) . |

\* cited by examiner

Primary Examiner—Bruce Snow
(74) Attorney, Agent, or Firm—Fulwider Patton Lee & Utecht, LLP (57) ABSTRACT

The invention is directed to an expandable stent for implantation in a body lumen, such as an artery. The stent consists of a plurality of radially expandable cylindrical elements generally aligned on a common longitudinal stent axis and interconnected by one or more interconnecting members placed so that the stent is flexible in the longitudinal direction.

13 Claims, 6 Drawing Sheets

FLEXIBLE STENT AND METHOD OF USE

BACKGROUND OF THE INVENTION

This invention relates to expandable endoprosthesis devices, generally known as stents, which are designed for implantation in a patient s body lumen, such as blood vessels to maintain the patency thereof. These devices are particularly useful in the treatment and repair of blood vessels after a stenosis has been compressed by percutaneous transluminal coronary angioplasty (PTCA), or percutaneous transluminal angioplasty (PTA), or removed by atherectomy or other means.

Stents are generally cylindrically-shaped devices which function to hold open and sometimes expand a segment of a blood vessel or other lumen such as a coronary artery. They are particularly suitable for use to support the lumen or hold back a dissected arterial lining which can occlude the fluid passageway therethrough.

A variety of devices are known in the art for use as stents and have included coiled wires in a variety of patterns that are expanded after being placed intraluminally on a balloon catheter; helically wound coiled springs manufactured from an expandable heat sensitive metal; and self expanding stents inserted in a compressed state and shaped in a zigzag pattern. One of the difficulties encountered using prior stents involved maintaining the radial rigidity needed to hold open a body lumen while at the same time maintaining the longitudinal flexibility of the stent to facilitate its delivery and accommodate the often tortuous path of the body lumen.

Another problem area has been the limiting range of expandability. Certain prior art stents expand only to a limited degree due to the uneven stresses created upon the stents during radial expansion. This necessitates providing stents with a variety of diameters, thus increasing the cost of manufacture. Additionally, having a stent with a wider range of expandability allows the physician to redilate the stent if the original vessel size was miscalculated.

Another problem with the prior art stents has been contraction of the stent along its longitudinal axis upon radial expansion of the stent. This can cause placement problems within the artery during expansion.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter.

What has been needed is a stent which has an enhanced degree of flexibility so that it can be readily advanced through tortuous passageways and radially expanded over a wider range of diameters with minimal longitudinal contraction to accommodate a greater range of vessel diameters, all with minimal longitudinal contraction. The expanded stent must also of course have adequate structural strength (hoop strength) to hold open the body lumen in which it is expanded. The present invention satisfies this need.

SUMMARY OF THE INVENTION

The present invention is directed to stents of enhanced longitudinal flexibility and configuration which permit the stents to expand radially to accommodate a greater number of different diameter vessels, both large and small, than heretofore was possible. The stents of the instant application also have greater flexibility along their longitudinal axis to facilitate delivery through tortuous body lumens, but remain highly stable when expanded radially, to maintain the patency of a body lumen such as an artery or other vessel when implanted therein. The unique patterns of the stents of the instant invention permit both greater longitudinal flexibility and enhanced radial expansibility and stability compared to prior art stents.

Each of the different embodiments of stents of the present invention include a plurality of adjacent cylindrical elements which are generally expandable in the radial direction and arranged in alignment along a longitudinal stent axis. The cylindrical elements are formed in a variety of serpentine wave patterns transverse to the longitudinal axis and containing a plurality of alternating peaks and valleys. At least one interconnecting member extends between adjacent cylindrical elements and connects them to one another. These interconnecting members insure minimal longitudinal contraction during radial expansion of the stent in the body vessel. The serpentine patterns contain varying degrees of curvature in regions of the peaks and valleys and are adapted so that radial expansion of said cylindrical elements are generally uniform around their circumferences during expansion of the stents from their contracted conditions to their expanded conditions.

The resulting stent structures are a series of radially expandable cylindrical elements which are spaced longitudinally close enough so that small dissections in the wall of a body lumen may be pressed back into position against the lumenal wall, but not so close as to compromise the longitudinal flexibility of the stent both when being negotiated through the body lumens in their unexpanded state and when expanded into position. The serpentine patterns allow for an even expansion around the circumference by accounting for the relative differences in stress created by the radial expansion of the cylindrical elements. Each of the individual cylindrical elements may rotate slightly relative to their adjacent cylindrical elements without significant deformation, cumulatively providing stents which are flexible along their length and about their longitudinal axis, but which are still very stable in the radial direction in order to resist collapse after expansion.

Each of the stents of the invention can be readily delivered to the desired lumenal location by mounting them on an expandable member of a delivery catheter, for example a balloon, and passing the catheter-stent assembly through the body lumen to the implantation site. A variety of means for securing the stents to the expandable member on the catheter for delivery to the desired location is available. It is presently preferred to compress the stent onto the unexpanded balloon. Other means to secure the stent to the balloon include providing ridges or collars on the inflatable member to restrain lateral movement, using bioabsorbable temporary adhesives, or a retractable sheath to cover the stent during delivery through a body lumen.

The presently preferred structures for the expandable cylindrical elements which form the stents of the present invention generally have a circumferential serpentine pattern containing a plurality of alternating peaks and valleys. The degrees of curvature along adjacent peaks and valleys are designed to compensate for the stresses created during expansion of the stent so that expansion of each of the peaks and valleys is uniform relative to one another. This novel structure permits the stents to radially expand from first smaller diameters to any number of second larger diameters since stress is distributed more uniformly along the cylindrical elements. This uniformity in stress distribution reduces the tendency of stress fractures in one particular region and allows high expansion rates.

The different stent embodiments also allow the stents to expand to various diameters from small to large to accommodate different-sized body lumens, without loss of radial strength and limited contraction of longitudinal length. The open reticulated structure of the stents provides low mass allowing for the perfusion of blood over a large portion of the arterial wall which can improve the healing and repair of a damaged arterial lining.

In one presently preferred embodiment, the ability of the stent to treat larger diameter vessels results from increasing the number of units of the repeating pattern of peaks and valleys so that the starting compressed diameter is larger than in prior art devices. When expanded, the stent of this embodiment has sufficient coverage of the luminal wall and maintains structural integrity in resisting collapse due to forces imposed by the lumenal wall.

The serpentine patterns of the cylindrical elements can have different degrees of curvature of adjacent peaks and valleys to compensate for the expansive properties of the peaks and valleys. Additionally, the degree of curvature along the peaks can be set to be different in immediately adjacent areas to compensate for the expansive properties of the valleys adjacent to it. The more even radial expansion of this design results in stents which can be expanded to accommodate larger diameters with minimal out of plane twisting since the high stresses are not concentrated in any one particular region of the pattern, but are more evenly distributed among the peaks and valleys, allowing them to expand uniformly. Reducing the amount of out of plane twisting also minimizes the potential for thrombus formation. The serpentine pattern of the individual cylindrical elements can be in phase which each other in order to reduce contraction of the stents along their length when expanded. The cylindrical elements of the stents are plastically deformed when expanded (except with NiTi alloys) so that the stents will remain in the expanded condition and therefore they must be sufficiently rigid when expanded to prevent the collapse thereof in use.

With stents formed from super-elastic nickel-titanium (NiTi) alloys, the expansion occurs when the stress of compression is removed. This allows the phase transformation from martensite back to austenite to occur, and as a result the stent expands.

After the stents are expanded some of the peaks and/or valleys may, but not necessarily, tip outwardly and embed in the vessel wall. Thus, after expansion, the stents may not have a smooth outer wall surface, rather they have small projections which embed in the vessel wall and aid in retaining the stents in place in the vessel. The tips projecting outwardly and strut twisting are due primarily to the struts having a high aspect ratio. In one preferred embodiment, the strut width is about 0.0035 inch and a thickness of about 0.0022 inch, providing an aspect ratio of 1.6. An aspect ratio of 1.0 will produce less tipping and twisting.

The elongated interconnecting members which interconnect adjacent cylindrical elements should have a transverse cross-section similar to the transverse dimensions of the undulating components of the expandable cylindrical members. The interconnecting members may be formed in a unitary structure with the expandable cylindrical elements formed from the same intermediate product, such as a tubular element, or they may be formed independently and mechanically secured between the expandable cylindrical elements.

Preferably, the number and location of the interconnecting members can be varied in order to develop the desired longitudinal flexibility in the stent structure both in the unexpanded as well as the expanded condition. These properties are important to minimize alteration of the natural physiology .of the body lumen into which the stent is implanted and to maintain the compliance of the body lumen which is internally supported by the stent. Generally, the greater the longitudinal flexibility of the stents, the easier and the more safely they can be delivered to the implantation site, especially where the implantation site is on a curved section of a body lumen, such as a coronary artery or a peripheral blood vessel, and especially saphenous veins and larger vessels.

Thus, in one preferred embodiment, a maximum number of interconnecting members are provided to connect the end cylindrical elements, while a minimum number of interconnecting members connect the cylindrical elements of the center of the stent. Thus, the ends are fully supported and have more mass than the center section. The center section of the stent has less mass and is highly flexible, allowing the stent to navigate very tortuous vessels during delivery.

Other features and advantages of the present invention will become more apparent from the following detailed description of the invention, when taken in conjunction with the accompanying exemplary drawings.

DETAILED DESCRIPTION OF THE PREFERRED EMBODIMENTS

With respect to prior art stent designs, such as the MultiLink Stent™ manufactured by Advanced Cardiovascular Systems, Inc., Santa Clara, Calif., a plurality of cylindrical rings are connected by three connecting members between adjacent cylindrical rings. Each of the cylindrical rings is formed of a repeating pattern of U-, Y-, and W-shaped members, typically having three repeating patterns forming each cylindrical ring. A more detailed discussion of the configuration of the MultiLink Stent™ can be found in U.S. Pat. No. 5,569,295 (Lam) and U.S. Pat. No. 5,514,154 (Lau et al.).

In order to provide a highly flexible stent adapted for insertion in larger vessels, and having the ability to provide better coverage of the luminal wall without sacrificing radial strength or flexibility, the stent of the present invention adds at least one more repeating pattern of U-, Y-, and W-shaped members to each cylindrical ring. Further, two connecting members, spaced 180° apart, between adjacent cylindrical rings, provides for increased flexibility over the prior art stents, which is essential for delivering the stent through tortuous anatomy and implanting it in a curved section of vessel.

Figure 1:
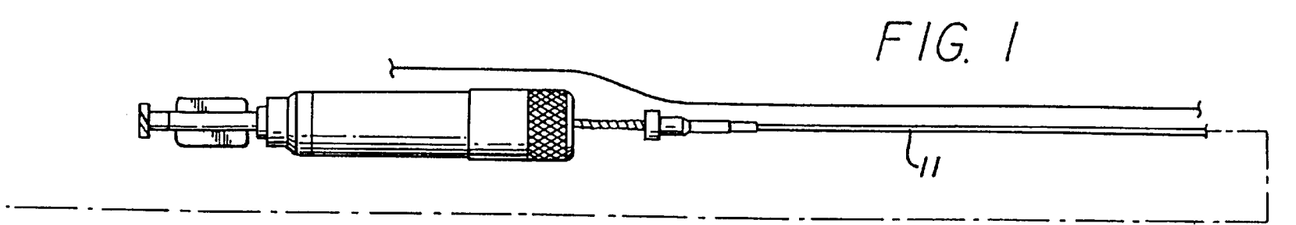
FIG. 1 is an elevational view, partially in section, depicting the stent embodying features of the invention mounted on a delivery catheter and disposed within a vessel.

FIG. 1 illustrates a first embodiment of stent 10 incorporating features of the invention which is mounted onto a delivery catheter 11. The stent generally comprises a plurality of radially expandable cylindrical elements 12 disposed generally coaxially and interconnected by interconnection members 13 disposed between adjacent cylindrical elements 12. The delivery catheter 11 has an expandable portion or balloon 14 for expanding stent 10 within an artery 15 or other vessel. The artery 15, as shown in FIG. 1, has a dissected lining 16 which has occluded a portion of the arterial passageway.

The delivery catheter 11 onto which stent 10 is mounted, is essentially the same as a conventional balloon dilatation catheter for angioplasty procedures. The balloon 14 may be formed of suitable materials such as polyethylene, polyethylene terephthalate, polyvinyl chloride, nylon and inomers such as Surlyn® manufactured by the Polymer Products Division of the Du Pont Company. Other polymers may also be used. In order for stent 10 to remain in place on balloon 14 during delivery to the site of the damage within artery 15, stent 10 is compressed onto the balloon. A retractable protective delivery sleeve 20 may be provided to further ensure that the stents stay in place on the expandable portion of delivery catheter 11 and prevent abrasion of the body lumen by the open surface of stent 10 during delivery to the desired arterial location. Other means for securing stent 10 onto balloon 14 also may be used, such as providing collars or ridges on the ends of the working portion, i.e., the cylindrical portion, of balloon 14. Each radially expandable cylindrical element 12 of stent 10 may be independently expanded, therefore balloon 14 may be provided with an inflated shape other than cylindrical, e.g., tapered, to facilitate implantation of stent 10 in a variety of body lumen shapes.

Figure 2:
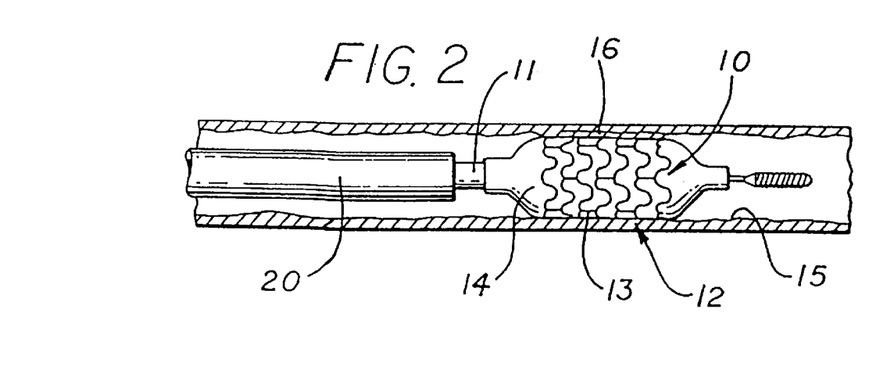
FIG. 2 is an elevational view, partially in section, similar to that shown in FIG. 1, wherein the stent is expanded within a vessel, pressing the lining against the vessel wall.

In a preferred embodiment, the delivery of stent 10 is accomplished in the following manner. Stent 10 is first mounted onto inflatable balloon 11 on the distal extremity of the delivery catheter 11. Stent 10 may be "crimped" down onto the balloon to ensure a low profile. The catheter-stent assembly can be introduced within the patient's vasculature in a conventional Seldinger technique through a sliding catheter (not shown). Guidewire 18 is disposed through the damaged arterial section with the detached or dissected lining 16 and then the catheter-stent assembly is advanced over the guidewire 18 within artery 15 until the stent 10 is directly under the detached lining 16. Balloon 14 of the catheter 11 is expanded, expanding stent 10 against the inside of artery 15, which is illustrated in FIG. 2. While not shown in the drawing, artery 15 is preferably expanded slightly by the expansion of stent 10 to seat or otherwise fix the stent 10 to prevent movement. In some circumstances during the treatment of stenotic portions of an artery, the artery may have to be expanded considerably in order to facilitate passage of blood or other fluid therethrough. While FIGS. 1–3 depict a vessel having detached lining 16, stent 10 can be used for purposes other than repairing the lining, such as supporting the vessel, reducing the likelihood of restenosis, or to assist in attaching a vascular graft (not shown) when repairing an aortic abdominal aneurysm.

Figure 3:
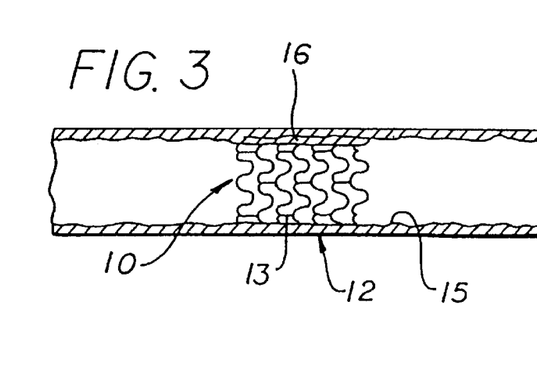
FIG. 3 is an elevational view, partially in section, showing the expanded stent within the vessel after withdrawal of the delivery catheter.

Stent 10 serves to hold open artery 15 after catheter 11 is withdrawn, as illustrated in FIG. 3. Due to the formation of stent 10 from an elongated tubular member, the undulating component of the cylindrical elements of stent 10 is relatively flat in transverse cross-section, so that when the stent is expanded, the cylindrical elements are pressed into the wall of artery 15 and as a result do not interfere with the blood flow through artery 15. Cylindrical elements 12 of stent 10 which are pressed into the wall of artery 15 will eventually be covered with endothelial cell growth which further minimizes blood flow turbulence. The serpentine pattern of cylindrical sections 12 provide good tacking characteristics to prevent stent movement within the artery. Furthermore, the closely spaced cylindrical elements 12 at regular intervals provide uniform support for the wall of artery 15, and consequently are well adapted to tack up and hold in place small flaps or dissections in the wall of artery 15 as illustrated in FIGS. 2 and 3.

Figure 4:
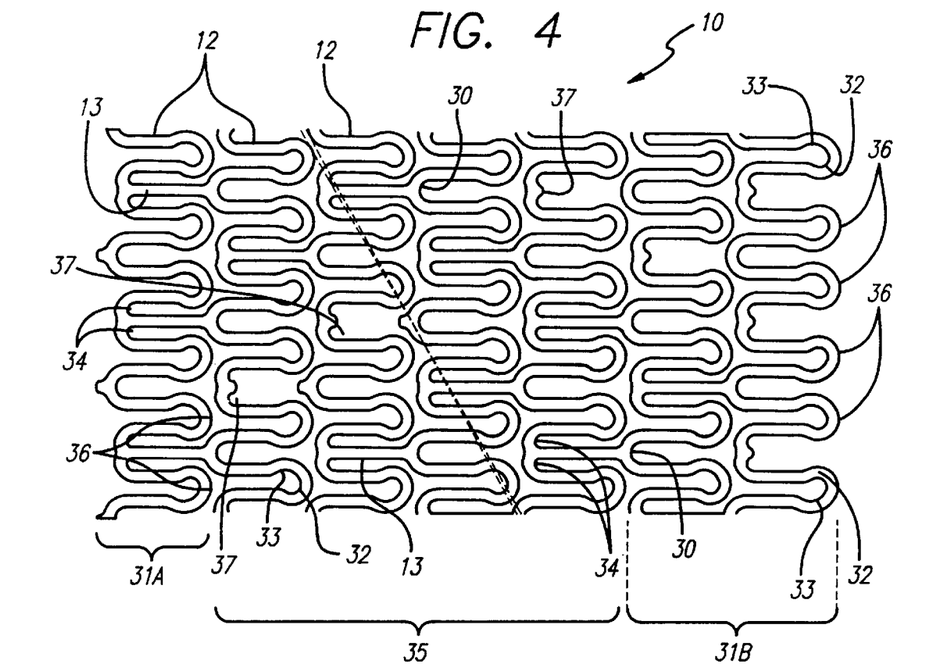
FIG. 4 is a plan view of a flattened section of one embodiment of a stent of the invention which illustrates the serpentine pattern and the varying number of interconnecting members of the stent.
Figure 5:
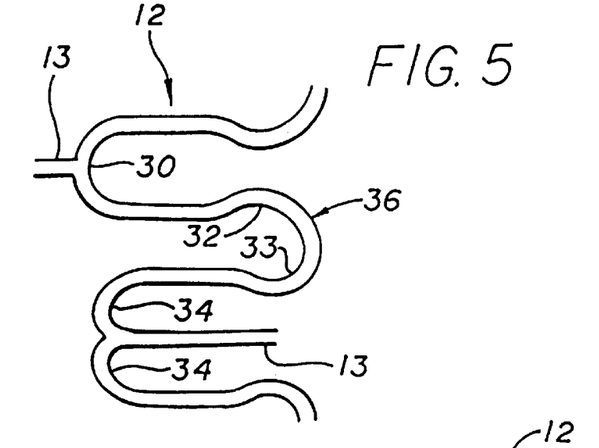
FIG. 5 is an enlarged partial view of the stent of FIG. 4 depicting the serpentine pattern along the peaks and valleys that form the cylindrical elements of the stent.

In one preferred embodiment of stent 10, as depicted in FIGS. 4 and 5, the stresses involved during expansion from a low profile to an expanded profile are much more evenly distributed among the various peaks and valleys of stent 10. As seen in FIG. 4, a portion of cylindrical element 12 of stent 10 illustrates the serpentine pattern having a plurality of peaks and valleys which aid in the even distribution of expansion forces. In this first embodiment, interconnecting members 13 serve to connect adjacent peaks and valleys of each adjacent cylindrical element 12 as described above. The various peaks and valleys generally have U, Y and W shapes, in a repeating pattern to form cylindrical element 13. During expansion, double-curved portions (W) 34 located in the region of the valley where interconnecting members 13 are connected, have the most mass and accordingly are the stiffest structure during deformation, while peak portions (U) 36 are the least stiff, and valley portions (Y) 30 have an intermediate stiffness. In this FIG. 4 embodiment, there are three repeating patterns of peaks and valleys in each cylindrical element 12, which allows the stent to be crimped to a very small profile.

The stent can be viewed in FIG. 4 as having three sections, first and second end sections 31A,31B and center section 35. As is shown, the end sections have interconnecting members 13 in each W or double-curved portion 34, thereby providing maximum support in each end of the stent.

In order to improve flexibility and more uniform expansion, every second interconnecting member 13 is removed from certain cylindrical elements as shown by members 37. Thus, with interconnecting member 13 removed from member 37 in center section 35, there is less mass, and hence less stiffness, which affords a more flexible and uniform, even expansion. Adjacent cylindrical elements 12 are thus connected by only two interconnecting elements 13, which provides for a highly flexible stent. The interconnecting members 13 are positioned 120° apart on the stent. Importantly, stent 10 of FIGS. 2–5 has an expansion ratio from the crimped to expanded configuration in the range of about 1.0 to 5.0, while maintaining structural integrity when expanded.

Because of the design, the double curved portion 34 is the stiffest structure and peak portion 36 is the least stiff structure, which accounts for the different stresses arising during expansion. Also, the least stiff structure, peak portion 36, is positioned between double curved portion 34 and valley portion 30, which are comparatively stiffer structures. To even out the stresses, peak portion 36 has different curvatures at regions 32 and 33. Region 33 has a larger radius than region 32 and will expand more easily. Since region 32 is adjacent the stiffer area of double curved portion 34, both region 32 and double curved portion 34 will expand more uniformly and more evenly distribute the expansion stresses. Further, valley portion 30 and double curved portion 34 also have different diameters to even out the expansion forces in relation to peak portion 36. Due to the novel structure as described, the shortcomings of the prior art, which include out of plane twisting of the metal, is avoided. These differing degrees of curvature along the peak portion 36 allow for the more even expansion of the cylindrical element 12 as a whole.

Figure 6:
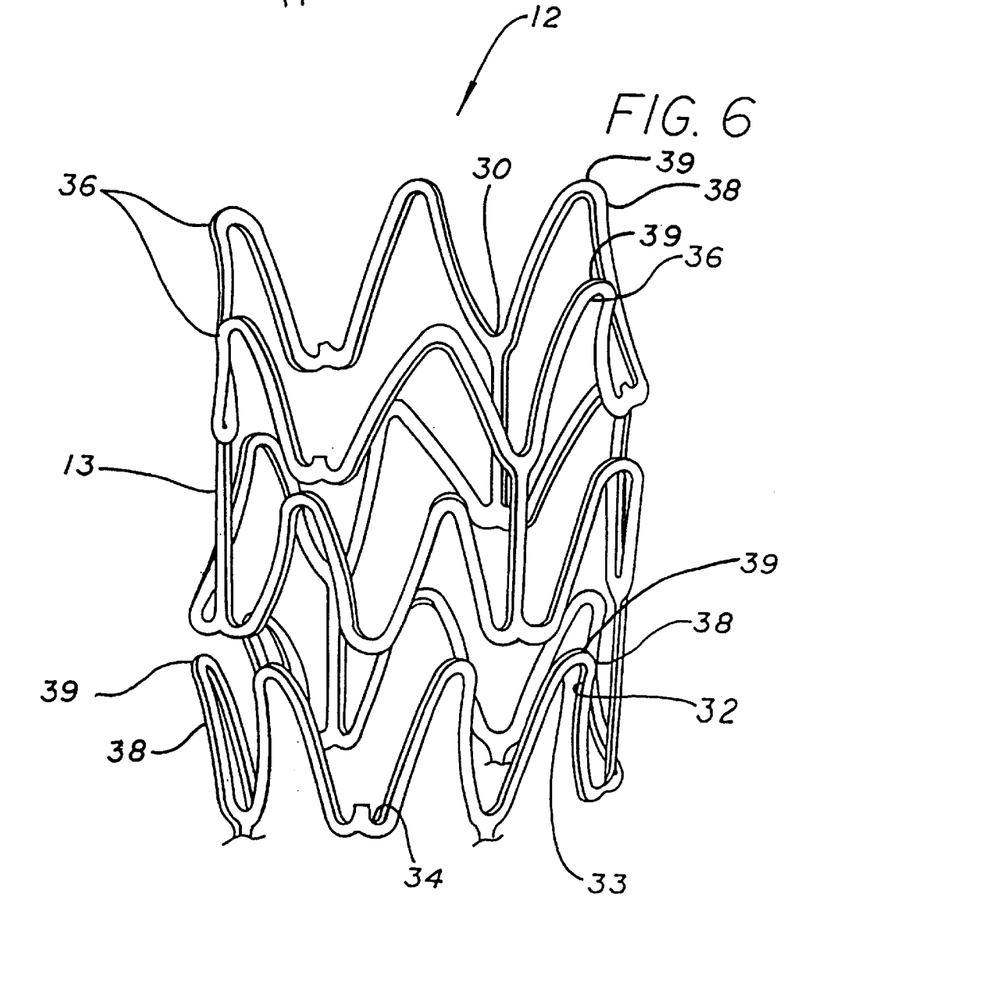
FIG. 6 is a perspective view of the stent of FIG. 4 in the expanded configuration.

Referring to FIG. 6, after expansion, portions of the various elements may turn outwardly, forming small projections 38 which will embed in the vessel wall. For example, the tip 39 of peak portion 36 tilts outwardly upon expansion a sufficient amount to embed into the vessel wall and help secure the implanted stent 10. Upon expansion, projections 38 provide an outer wall surface on the stent that is not smooth, but instead has a plurality of projections 38 all along the outer wall surface. While projections 38 assist in securing stent 10 in the vessel wall, they are not sharp so as to cause trauma or damage to the vessel wall. The tips projecting outwardly and strut twisting are due primarily to the struts having a high aspect ratio. In one preferred embodiment, the strut width is about 0.0035 inch and a thickness of about 0.0022 inch, providing an aspect ratio of 1.6. An aspect ratio of 1.0 will produce less tipping and twisting.

Referring to FIGS. 7–11, additional preferred embodiments of stents of the invention are shown. The embodiment of stent 40 of FIGS. 7A and 7B and 8 have the common features of four repeating serpentine wave pattern sections 43 and four interconnecting members 42 for each cylindrical member 41. All of the arcs 39a, 39b, 39c, and 39d of FIG. 8 have the same radius of curvature providing a simplified single arc pattern. In contrast, all of the arcs of FIG. 7B have different radii of curvature. Stent 40 has a plurality of cylindrical members 41 that are connected by interconnecting members 42. Each cylindrical member 41 is made of four repeating serpentine wave pattern sections 43 with a valley portion 44, a peak portion 45, and double curve portion 46. The valley portion 44 and peak portion 45 each have a generally single radius of curvature. The valley portion 44 is connected at both of its end areas 47 to linking portions 48 which bridge to first ends 49 of peak portions 45. The linking portions 48 are generally straight and elongate.

Figure 7A:
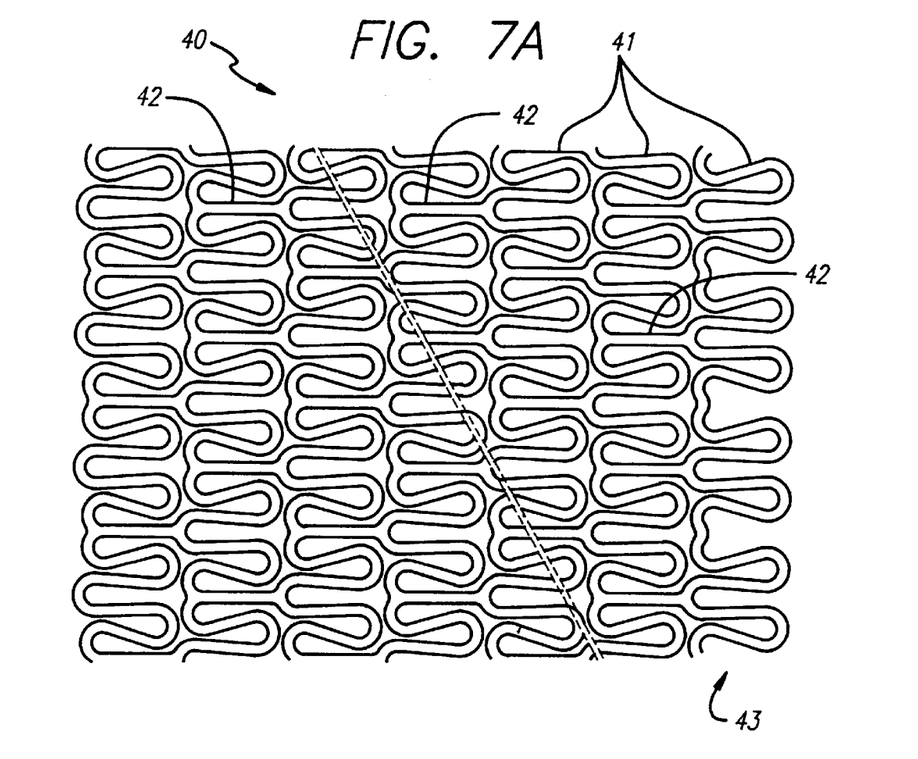
FIG. 7A is a plan view of a flattened section of another embodiment of the stent of the invention illustrating four repeating patterns for each cylindrical ring or element.
Figure 8:
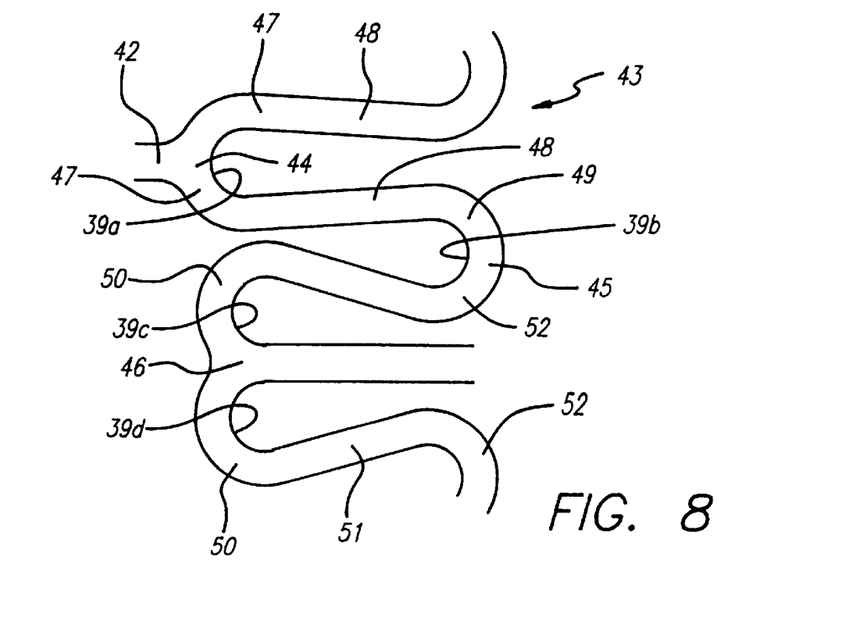
FIG. 8 is an enlarged partial view of the stent of FIG. 7 depicting the serpentine wave pattern along peaks and valleys that form the cylindrical elements of the stent.

As depicted in FIGS. 7A and 8, opposite end regions 50 of double curved portions 46 are connected to link members 51 which connect to second ends 52 of peak portion 45. The ends of link members 51 connected to opposite ends 50 of double curved portion 46 lie closer in its unexpanded state to link portions 48 than the opposite ends of link member 51 connected to peak portion 45 at its second end 52—link members 51 are offset diagonally to the longitudinal axis of the stent. As noted above, interconnecting members 42 connect together adjacent cylindrical member 41. These interconnecting members 42 preferably extend away from valley portions 44 and its connected link portions 48 and extend between two link members 51 of an adjacent double curve portion 46 to join double curve portion 46 between its two ends 49. The design of stent 40 thus will allow a great range of expansion to enlarge the diameter thereof, such as 1.0 to 4.0 times the original diameter, or even more.

Figure 7B:
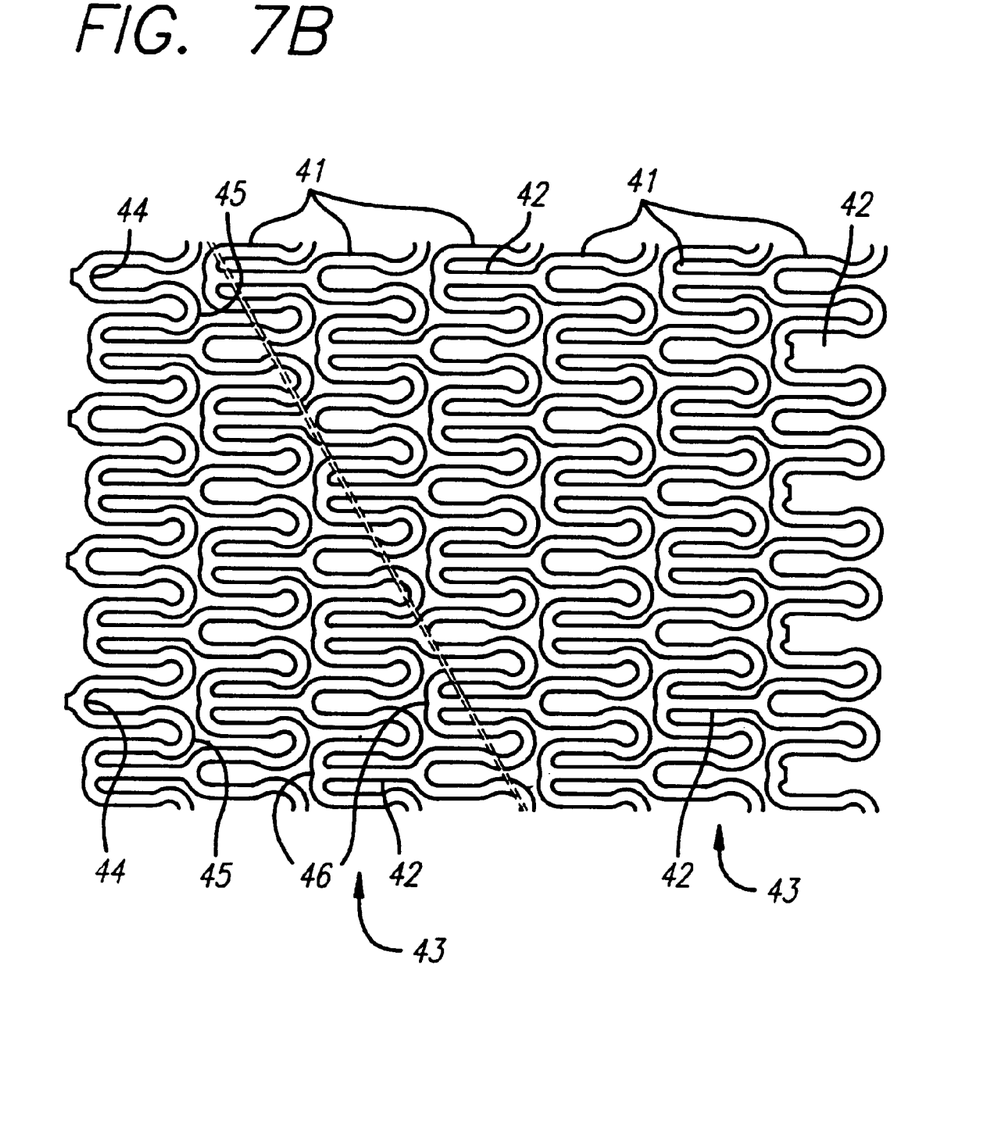
FIG. 7B is a plan view of a flattened section of another embodiment of the stent of the invention depicting four repeating patterns, and four connecting members between the cylindrical elements, and having varying degrees of curvature in the U-shaped sections.
Figure 9:
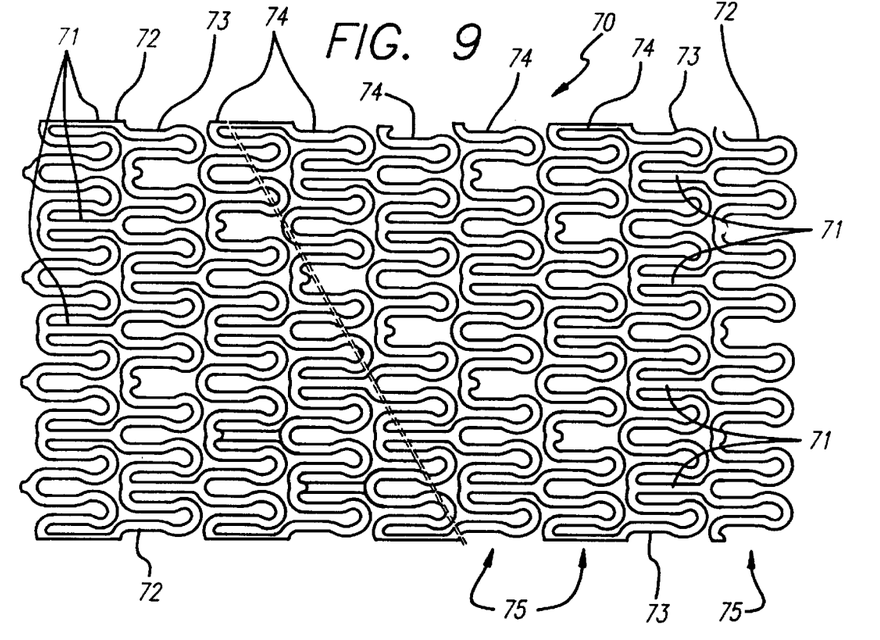
FIG. 9 is a plan view of a flattened section of another embodiment of the stent of the invention which illustrates the serpentine pattern of the stent with a decreased number of interconnecting members.

Stent 70 of FIG. 9 depicts another embodiment and is similar the stent of FIG. 7B, except that it retains all interconnecting members 71 to connect cylindrical elements 73 to cylindrical element 72. In the center cylindrical elements 74, some interconnecting members are removed and preferably alternating interconnecting members are removed in center cylindrical elements 74 which lie between terminating cylindrical elements 72. Each cylindrical element 72,73 and 74 has four repeating serpentine wave patterns 75 which provides for maximum expansion ratio, such as for implanting in a saphenous vein.

Figure 10:
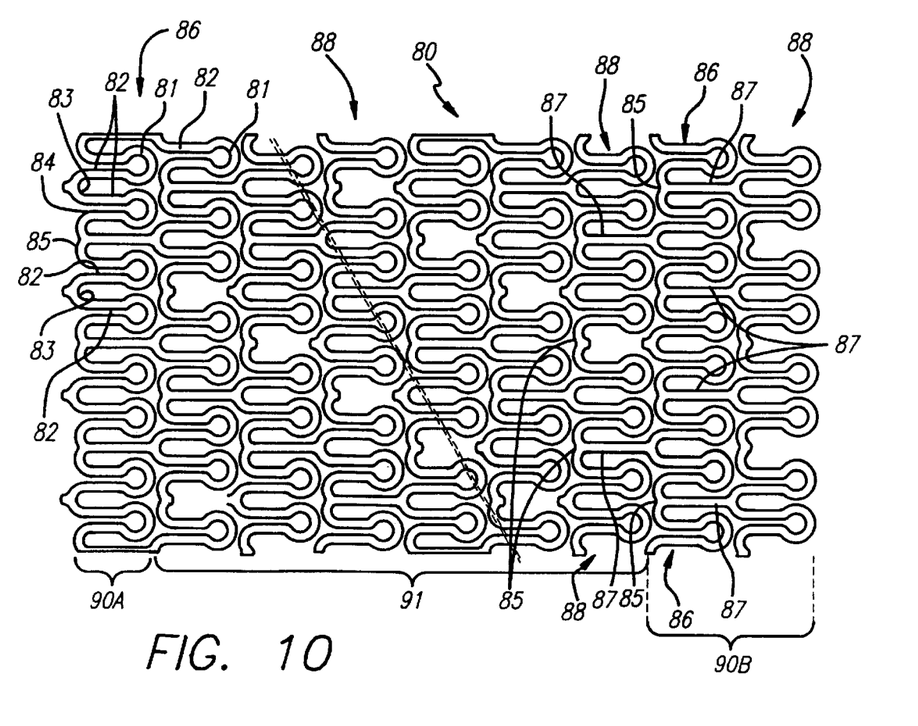
FIG. 10 is a plan view of a flattened section of another embodiment of the stent of the invention which illustrates the serpentine pattern of the stent with a decreased number of interconnections in the center section of the stent.

Referring to FIG. 10, another preferred embodiment of stent 80 is shown, where the curvature of peaks 81 are somewhat circular and circumscribe more than 180 degrees of curvature, for example about 240 degrees of curvature, while remaining preferably symmetrical. The radius and degree of arc can vary to provide for optimal expansion and crimping. In its unexpanded state, linking portions 82 connecting peaks 81 to valleys 83 and link member 84 connecting peak 81 to double curved portions 85 generally are parallel to each other. In cylindrical members 86, which form end sections 90A,90B, there is an interconnecting element 87 in each double curved portion 85. In cylindrical elements 88, which are in flexible center section 91, there is an interconnecting member 86 in every other double curved portion 85. This configuration provides a stent 80 that has less mass in the center section and is more flexible than prior art stent structures, yet the end sections are still relatively stiff and provide substantial support. The four repeating serpentine wave patterns in each cylindrical element 86,88 provide maximum radial expansion, structural integrity, and vessel coverage.

Figure 11:
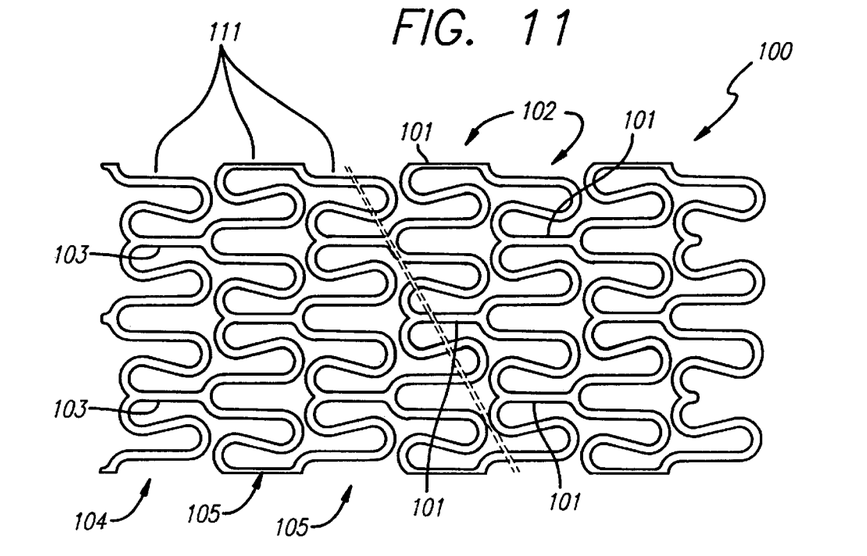
FIG. 11 is a plan view of a flattened section of a another embodiment of the stent of the invention which illustrates the serpentine pattern of the stent.

FIG. 11 depicts another embodiment of stent 100 having only two interconnecting members 101 connecting adjacent cylindrical members 102 in the center of the stent and two interconnecting members 103 are used at terminating cylindrical elements 104. This configuration again provides a much higher degree of flexibility not found in prior art stents. Stent 100 also has fewer repeating serpentine elements 105 per each cylindrical element 111 and has a more open pattern to allow for more extensive crimping to reduce its diameter further to ensure a very low delivery profile. Stent 100 is ideally suited for placement in vessels having a diameter in the 2.0 to 3.0 mm (0.079 to 0.11 inch) range. Each cylindrical element 102 has two repeating serpentine wave patterns 105 which can be crimped to very small profiles for delivery in smaller vessels.

It should be understood that the term "interconnecting members" as used herein can include not only those connecting elements specifically depicted in the drawings, but also include welds between adjacent cylindrical elements or simply an uncut area between cylindrical elements.

Stents 10, 40, 70, 80, and 100 depicted in the drawing figures are shown with the center cut of the laser, but after subtracting the kerf width and then polishing, the valley and peak portions, link portions, link members, and interconnecting portions will have slightly narrower widths than as depicted. Further, in many of the drawing figures the stent is depicted flat, in a plan view, for ease of illustration. All of the embodiments depicted herein are cylindrically-shaped stents that are generally formed from tubing by laser cutting as will be described.

One important feature of all of the embodiments of the present invention is the capability of the stents to expand from a low-profile diameter to a diameter much greater than heretofore was available, while still maintaining structural integrity in the expanded state and remaining highly flexible. Due to the novel structures, the stents of the present invention each have an overall expansion ratio of about 1.0 up to about 4.0 times the original diameter, or more, using certain compositions of stainless steel. For example, a 316L stainless steel stent of the invention can be radially expanded from a diameter of 1.0 unit up to a diameter of about 4.0 units, which deforms the structural members beyond the elastic limit. The stents still retain structural integrity in the expanded state and will serve to hold open the vessel in which they are implanted. Materials other than stainless steel (316L) may afford higher or lower expansion ratios without sacrificing structural integrity.

The stents of the present invention can be made in many ways. However, the preferred method of making the stent is to cut a thin-walled tubular member, such as stainless steel tubing to remove portions of the tubing in the desired pattern for the stent, leaving relatively untouched the portions of the metallic tubing which are to form the stent. It is preferred to cut the tubing in the desired pattern by means of a machine-controlled laser.

The tubing may be made of suitable biocompatible material such as stainless steel. The stainless steel tube may be alloy-type: 316L SS, Special Chemistry per ASTM F138-92 or ASTMF139-92 grade 2. Special Chemistry of type 316L per ASTM F138-92 or ASTM F139-92 Stainless Steel for Surgical Implants in weight percent.

| | |
|---|---|
| Carbon (C) | 0.03% max. |
| Manganese (Mn) | 2.00% max. |
| Phosphorous (P) | .025% max. |
| Sulphur (S) | 0.010% max. |
| Silicon (Si) | 0.75% max. |
| Chromium (Cr) | 17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.2 inch or more. The wall thickness of the tubing is about 0.0003 inch.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished stent.

The process of cutting a pattern for the stent into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ laser set-up of the foregoing example. The program for control of the apparatus is dependent on the particular configuration used and the pattern to be ablated in the coding.

Cutting a fine structure (0.0034 inch web width) requires minimal heat input and the ability to manipulate the tube with precision. It is also necessary to support the tube yet not allow the stent structure to distort during the cutting operation. In order to successfully achieve the desired end results, the entire system must be configured very carefully. The tubes are made of stainless steel with an outside diameter of 0.060 inch to 0.066 inch and a wall thickness of 0.002 inch to 0.004 inch. These tubes are fixtured under a laser and positioned utilizing a CNC to generate a very intricate and precise pattern. Due to the thin wall and the small geometry of the stent pattern (0.0035 inch typical strut width), it is necessary to have very precise control of the laser, its power level, the focused spot size, and the precise positioning of the laser cutting path.

In order to minimize the heat input into the stent structure, which prevents thermal distortion, uncontrolled burn out of the metal, and metallurgical damage due to excessive heat, and thereby produce a smooth debris-free cut, a Q-switched Nd/YAG, typically available from Quantorix of Hauppauge, New York, that is frequency-doubled to produce a green beam at 532 nanometers is utilized. Q-switching produces very short pulses (<100 nS) of high peak powers (kilowatts), low energy per pulse ($\leq$3 mJ), at high pulse rates (up to 40 kHz). The frequency doubling of the beam from 1.06 microns to 0.532 microns allows the beam to be focused to a spot size that is two times smaller, therefore increasing the power density by a factor of four times. With all of these parameters, it is possible to make smooth, narrow cuts in the stainless steel tubes in very fine geometries without damaging the narrow struts that make up the stent structure. Hence, the system of the present invention makes it possible to adjust the laser parameters to cut narrow kerf width which will minimize the heat input into the material.

The positioning of the tubular structure requires the use of precision CNC equipment such as that manufactured and sold by Anorad Corporation. In addition, a unique rotary mechanism has been provided that allows the computer program to be written as if the pattern were being cut from a flat sheet. This allows both circular and linear interpolation to be utilized in programming.

The optical system which expands the original laser beam, delivers the beam through a viewing head and focuses the beam onto the surface of the tube, incorporates a coaxial gas jet and nozzle that helps to remove debris from the kerf and cools the region where the beam interacts with the material as the beam cuts and vaporizes the metal. It is also necessary to block the beam as it cuts through the top surface of the tube and prevent the beam, along with the molten metal and debris from the cut, from impinging on the opposite surface of the tube.

In addition to the laser and the CNC positioning equipment, the optical delivery system includes a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream that surrounds the focused beam and is directed along the beam axis. The coaxial gasjet nozzle (0.018 inch I.D.) is centered around the focused beam with approximately 0.010 inch between the tip of the nozzle and the tubing. The jet is pressurized with oxygen at 20 psi and is directed at the tube with the focused laser beam exiting the tip of the nozzle (0.018 inch dia.). The oxygen reacts with the metal to assist in the cutting process very similar to oxyacetylene cutting. The focused laser beam acts as an ignition source and controls the reaction of the oxygen with the metal. In this manner, it is possible to cut the material with a very fine kerf with precision.

In order to prevent burning by the beam and/or molten slag on the far wall of the tube I.D., a stainless steel mandrel (approx. 0.034 inch dia.) is placed inside the tube and is allowed to roll on the bottom of the tube as the pattern is cut. This acts as a beam/debris barrier protecting the far wall I.D.

Alternatively, this may be accomplished by inserting a second tube inside the stent tube which has an opening to trap the excess energy in the beam which is transmitted through the kerf along which collecting the debris that is ejected from the laser cut kerf. A vacuum or positive pressure can be placed in this shielding tube to remove the collection of debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied creating a small jet that would force the debris out of the laser cut kerf from the inside out. This would eliminate any debris from forming or collecting on the inside of the stent structure. It would place all the debris on the outside. With the use of special protective coatings, the resultant debris can be easily removed.

In most cases, the gas utilized in the jets may be reactive or non-reactive (inert). In the case of reactive gas, oxygen or compressed air is used. Oxygen is used in this application since it offers more control of the material removed and reduces the thermal effects of the material itself Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

The cutting process utilizing oxygen with the finely focused green beam results in a very narrow kerf (approximately 0.0005 inch) with the molten slag re-solidifying along the cut. This traps the cut-out scrap of the pattern requiring further processing. In order to remove the slag debris from the cut allowing the scrap to be removed from the remaining stent pattern, it is necessary to soak the cut tube in a solution of HCL for approximately eight minutes at a temperature of approximately 55° C. Before it is soaked, the tube is placed in a bath of alcohol/water solution and ultrasonically cleaned for approximately one minute to remove the loose debris left from the cutting operation. After soaking, the tube is ultrasonically cleaned in the heated HCL for one to four minutes depending upon the wall thickness. To prevent cracking/breaking of the struts attached to the material left at the two ends of the stent pattern due to harmonic oscillations induced by the ultrasonic cleaner, a mandrel is placed down the center of the tube during the cleaning/scrap removal process. At completion of this process, the stent structures are rinsed in water. They are now ready for electropolishing.

The stents are preferably electrochemically polished in an acidic aqueous solution such as a solution of ELECTRO-GLO #300, sold by the ELECTRO-GLO Co., Inc. in Chicago, Ill., which is a mixture of sulfuric acid, carboxylic acids, phosphates, corrosion inhibitors and a biodegradable surface active agent. The bath temperature is maintained at about 110–133° F. and the current density is about 0.4 to about 1.5 amps per $in^2$. Cathode to anode area should be at least about two to one. The stents may be further treated if desired, for example by applying a biocompatible coating.

Direct laser cutting produces edges which are essentially perpendicular to the axis of the laser cutting beam, in contrast with chemical etching and the like which produce pattern edges which are angled. Hence, the laser cutting process of the present invention essentially provides stent cross-sections, from cut-to-cut, which are square or rectangular, rather than trapezoidal. The resulting stent structure provides superior performance.

The stent tubing may be made of suitable biocompatible material such as stainless steel, titanium, tantalum, superelastic (nickel-titanium) NiTi alloys and even high strength thermoplastic polymers. The stent diameters are very small, so the tubing from which it is made must necessarily also have a small diameter. For PCTA applications, typically the stent has an outer diameter on the order of about 1.65 mm (0.065 inches) in the unexpanded condition, the same outer diameter of the hypotubing from which it is made, and can be expanded to an outer diameter of 5.08 mm (0.2 inches) or more. The wall thickness of the tubing is about 0.076 mm (0.003 inches). For stents implanted in other body lumens, such as PTA applications, the dimensions of the tubing are correspondingly larger. While it is preferred that the stents be made from laser cut tubing, those skilled in the art will realize that the stent can be laser cut from a flat sheet and then rolled up in a cylindrical configuration with the longitudinal edges welded to form a cylindrical member.

In the instance when the stents are made from plastic, the implanted stent may have to be heated within the arterial site where the stents are expanded to facilitate the expansion of the stent. Once expanded, it would then be cooled to retain its expanded state. The stent may be conveniently heated by heating the fluid within the balloon or the balloon itself directly by a known method.

The stents may also be made of materials such as superelastic (sometimes called pseudo-elastic) nickel-titanium (NiTi) alloys. In this case the stent would be formed full size but deformed (e.g. compressed) to a smaller diameter onto the balloon of the delivery catheter to facilitate intraluminal delivery to a desired intraluminal site. The stress induced by the deformation transforms the stent from an austenite phase to a martensite phase, and upon release of the force when the stent reaches the desired intraluminal location, allows the stent to expand due to the transformation back to the more stable austenite phase. Further details of how NiTi superelastic alloys operate can be found in U.S. Pat. No. 4,665,906 (Jervis) and U.S. Pat. No. 5,067,957 (Jervis), incorporated herein by reference in their entirety.

While the invention has been illustrated and described herein in terms of its use as intravascular stents, it will be apparent to those skilled in the art that the stents can be used in other instances in all vessels in the body. Since the stents of the present invention have the novel feature of expanding to very large diameters while retaining their structural integrity, they are particularly well suited for implantation in almost any vessel where such devices are used. This feature, coupled with limited longitudinal contraction of the stent when they are radially expanded, provide a highly desirable support member for all vessels in the body. Other modifications and improvements may be made without departing from the scope of the invention.

What is claimed is:

1. A longitudinally flexible stent for implanting in a body lumen and expandable from a contracted condition to an expanded condition, comprising:

a plurality of adjacent cylindrical elements each having a circumference extending around a longitudinal stent axis, the elements being arranged in cylindrical alignment along the longitudinal stent axis to form a generally tubular member;

the cylindrical elements formed in a generally serpentine wave pattern transverse to the longitudinal axis and containing alternating valley portions, peak portions and double-curved portions having the same radius of curvature, each cylindrical element being arranged so that the peaks of adjacent cylindrical elements are out of phase;

the generally tubular member having a first end section comprised of one cylindrical element, a second end section comprised of two cylindrical elements, a center section therebetween comprised of a plurality of cylindrical elements, four interconnecting members interconnecting the cylindrical elements of the center section, and five interconnecting members interconnecting the cylindrical element of each of the first and second end sections with the center section respectively; and whereby the center section is relatively more flexible than the first and the second end sections by including fewer interconnecting members in the center section than in each of the first and second end sections.

2. The stent of claim 1, wherein the center section includes adjacent cylindrical elements connected by two interconnecting members.

3. The stent of claim 1, wherein the interconnecting members connect the valley of one cylindrical element with a double curved portion of an adjacent cylindrical element.

4. The stent of claim 1, wherein the cylindrical members are configured for expanding from a first smaller diameter to a range of enlarged diameters without appreciable change in the length of the stent.

5. The stent of claim 1, wherein the stent is formed from a flat piece of material.

6. The stent of claim 1, wherein the stent is formed of a biocompatible material selected from the group consisting of stainless steel, tungsten, tantalum, super-elastic nickel-titanium alloys, and thermoplastic polymers.

7. The stent of claim 1, wherein the stent has a radial expansion ratio of about 1.0 in the contracted condition up to about 4.0 in the expanded condition.

8. The stent of claim 1, wherein the stent is formed from a single piece of tubing.

9. A longitudinally flexible stent for implanting in a body lumen and expandable from a contracted condition to an expanded condition, comprising:

a plurality of adjacent cylindrical elements each having a circumference extending around a longitudinal stent axis and each element being substantially independently expandable in the radial direction, each element being arranged in alignment along the longitudinal stent axis;

the cylindrical elements formed in a generally serpentine wave pattern transverse to the longitudinal axis and containing alternating valley portions, peak portions and double-curved portions having the same radius of curvature, each cylindrical element being arranged so that the peaks of adjacent cylindrical elements are out of phase;

a plurality of interconnecting members extending between the adjacent cylindrical elements and connecting valley portions and double-curved portions of adjacent cylindrical elements to one another; and the stent having a first end section comprised of one cylindrical element, a second end section comprised of two cylindrical elements, a center section therebetween comprised of a plurality of cylindrical elements, two interconnecting members interconnecting the cylindrical elements of the center section, and three interconnecting members interconnecting each of the first and second end sections with the center section, respectively;

whereby the center section is relatively more flexible than the first and the second end sections by including fewer interconnecting members in the center section than in each of the first and second end sections.

10. The stent of claim 9, wherein the cylindrical elements cooperate to define a generally smooth cylindrical surface and wherein the peak portions form projecting edges which project outwardly from the cylindrical surface upon expansion.

11. The stent of claim 9, wherein the stent is formed of a biocompatible material selected from the group consisting of stainless steel, tungsten, tantalum, super-elastic nickel-titanium alloys, and thermoplastic polymers.

12. The stent of claim 9, wherein said stent has a radial expansion ratio of about 1.0 in the contracted condition up to about 4.0 or more in the expanded condition.

13. The stent of claim 9, wherein the stent is formed from a single piece of tubing.

* * * * *